United States Patent
Sun et al.

(10) Patent No.: US 11,084,789 B2
(45) Date of Patent: Aug. 10, 2021

(54) MAST-CELL MODULATORS AND USES THEREOF

(71) Applicant: Beth Israel Deaconess Medical Center, Inc., Boston, MA (US)

(72) Inventors: Lijun Sun, Harvard, MA (US); Aristidis Veves, Quincy, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 16/738,371

(22) Filed: Jan. 9, 2020

(65) Prior Publication Data
US 2020/0148638 A1   May 14, 2020

Related U.S. Application Data

(62) Division of application No. 16/069,961, filed as application No. PCT/US2017/013279 on Jan. 13, 2017, now abandoned.

(60) Provisional application No. 62/278,722, filed on Jan. 14, 2016.

(51) Int. Cl.
| | |
|---|---|
| C07D 209/42 | (2006.01) |
| C07D 231/56 | (2006.01) |
| C07D 417/12 | (2006.01) |
| C07D 209/36 | (2006.01) |
| A61P 17/02 | (2006.01) |
| C07D 401/12 | (2006.01) |

(52) U.S. Cl.
CPC ............ C07D 209/42 (2013.01); A61P 17/02 (2018.01); C07D 209/36 (2013.01); C07D 231/56 (2013.01); C07D 401/12 (2013.01); C07D 417/12 (2013.01)

(58) Field of Classification Search
CPC ...... A61K 31/403; C07D 209/42; A61P 17/02
USPC ........................................................ 514/338
See application file for complete search history.

(56) References Cited

U.S. PATENT DOCUMENTS

| | | | |
|---|---|---|---|
| 6,353,015 | B1 | 3/2002 | Oxenkrug et al. |
| 6,500,853 | B1 | 12/2002 | Seehra et al. |
| 7,196,082 | B2 | 3/2007 | Doherty et al. |
| 7,547,720 | B2 | 6/2009 | Doherty et al. |
| 7,858,645 | B2 | 12/2010 | Ackermann et al. |
| 8,058,285 | B2 | 11/2011 | Reichelt et al. |
| 8,071,628 | B2 | 12/2011 | Ackermann et al. |
| 8,445,435 | B2 | 5/2013 | Shi |
| 8,445,437 | B2 | 5/2013 | Shi |
| 8,785,383 | B2 | 7/2014 | Shi |
| 2003/0195244 | A1 | 10/2003 | Hsieh et al. |
| 2004/0097575 | A1 | 5/2004 | Doherty et al. |
| 2005/0267108 | A1 | 12/2005 | Hsieh et al. |
| 2005/0267194 | A1 | 12/2005 | Hsieh et al. |
| 2007/0015771 | A1 | 1/2007 | Matteucci et al. |
| 2007/0191313 | A1 | 8/2007 | Beard et al. |
| 2008/0027111 | A1 | 1/2008 | Shi |
| 2008/0103182 | A1 | 5/2008 | Ackermann et al. |
| 2008/0160028 | A1 | 7/2008 | Reichelt et al. |
| 2009/0093511 | A1 | 4/2009 | Shi |
| 2010/0015093 | A1 | 1/2010 | Einav et al. |
| 2011/0245315 | A1 | 10/2011 | Chen et al. |
| 2011/0257196 | A1 | 10/2011 | Lu et al. |
| 2012/0071524 | A1 | 3/2012 | Lu et al. |
| 2012/0094987 | A1 | 4/2012 | Reichelt et al. |
| 2012/0129829 | A1 | 5/2012 | Sinha et al. |
| 2012/0214729 | A1 | 8/2012 | Son et al. |
| 2013/0197049 | A1 | 8/2013 | Li et al. |
| 2013/0231362 | A1 | 9/2013 | Shi |
| 2014/0329674 | A1 | 11/2014 | Woods et al. |
| 2015/0025443 | A1 | 1/2015 | Ray, II |

(Continued)

FOREIGN PATENT DOCUMENTS

| | | |
|---|---|---|
| DE | 10253426 A1 | 6/2004 |
| DE | 102004054666 A1 | 5/2006 |
| EP | 1532980 A1 | 5/2005 |

(Continued)

OTHER PUBLICATIONS

Hassan Y. Aboul-Enein et al Scavenging of reactive oxygen species by N-substitued indole-2 and 3-carboxamides. (Year: 2004).*

(Continued)

*Primary Examiner* — Rita J Desai
(74) *Attorney, Agent, or Firm* — McCarter & English, LLP (57) ABSTRACT

Provided are novel compounds of Formula I:

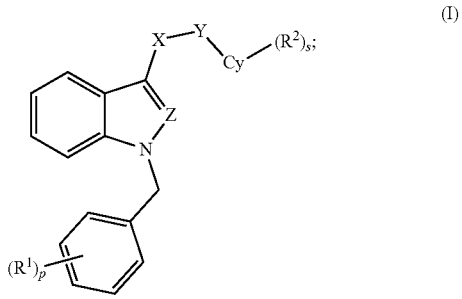

pharmaceutically acceptable salts thereof, and pharmaceutical compositions thereof, which are useful in the treatment of diseases and disorders associated with mast cells. Also provided are pharmaceutical compositions comprising the novel compounds of Formula I and methods for their use in treating one or more diseases and disorders associated with mast cells.

3 Claims, 2 Drawing Sheets

(56) References Cited

U.S. PATENT DOCUMENTS

| | | | |
|---|---|---|---|
| 2018/0161388 A1 | 6/2018 | Sun et al. | |
| 2019/0016680 A1 | 1/2019 | Sun et al. | |

FOREIGN PATENT DOCUMENTS

| | | | | |
|---|---|---|---|---|
| FR | 2875230 | A1 | 3/2006 | |
| WO | 1993/10094 | A1 | 5/1993 | |
| WO | 1996/32379 | A1 | 10/1996 | |
| WO | 1999/23070 | A1 | 5/1999 | |
| WO | 1999/33800 | A1 | 7/1999 | |
| WO | 1999/055696 | A1 | 11/1999 | |
| WO | 2000/012045 | A2 | 3/2000 | |
| WO | 2001/049688 | A1 | 7/2001 | |
| WO | 2001/057024 | A1 | 8/2001 | |
| WO | 2001/058869 | A2 | 8/2001 | |
| WO | 2002/060426 | A2 | 8/2002 | |
| WO | 2003/000253 | A1 | 1/2003 | |
| WO | 2003/035005 | A2 | 5/2003 | |
| WO | 2004/006920 | A1 | 1/2004 | |
| WO | 2004/089415 | A2 | 10/2004 | |
| WO | 2004/089416 | A2 | 10/2004 | |
| WO | 2004/089470 | A2 | 10/2004 | |
| WO | 2006/010008 | A1 | 1/2006 | |
| WO | 2006/015263 | A2 | 2/2006 | |
| WO | 2006/015283 | A2 | 2/2006 | |
| WO | WO-2006015263 | A2 * | 2/2006 | ........... C07D 333/72 |
| WO | 2006/025069 | A2 | 3/2006 | |
| WO | 2006/060535 | A2 | 6/2006 | |
| WO | 2006/129178 | A1 | 12/2006 | |
| WO | 2006/133353 | A2 | 12/2006 | |
| WO | 2007/011647 | A2 | 1/2007 | |
| WO | 2007/022321 | A2 | 2/2007 | |
| WO | 2007/025613 | A2 | 3/2007 | |
| WO | 2007/062399 | A2 | 5/2007 | |
| WO | 2007/095561 | A2 | 8/2007 | |
| WO | 2007/109362 | A2 | 9/2007 | |
| WO | 2007/112322 | A2 | 10/2007 | |
| WO | 2008/009415 | A2 | 1/2008 | |
| WO | 2008/019357 | A2 | 2/2008 | |
| WO | WO-2008019357 | A2 * | 2/2008 | .............. A61P 19/06 |
| WO | 2008/027340 | A2 | 3/2008 | |
| WO | 2008/027341 | A2 | 3/2008 | |
| WO | 2008/036967 | A2 | 3/2008 | |
| WO | 2008/048981 | A2 | 4/2008 | |
| WO | 2008/071451 | A1 | 6/2008 | |
| WO | 2008/089015 | A1 | 7/2008 | |
| WO | 2008/100867 | A2 | 8/2008 | |
| WO | 2008/141013 | A1 | 11/2008 | |
| WO | 2008/157740 | A2 | 12/2008 | |
| WO | 2009/023623 | A1 | 2/2009 | |
| WO | 2009/106980 | A2 | 9/2009 | |
| WO | 2009/106982 | A1 | 9/2009 | |
| WO | 2009/108551 | A2 | 9/2009 | |
| WO | 2009/117335 | A2 | 9/2009 | |
| WO | 2009/121033 | A2 | 10/2009 | |
| WO | 2009/121623 | A2 | 10/2009 | |
| WO | 2010/129553 | A1 | 11/2010 | |
| WO | 2011/049988 | A2 | 4/2011 | |
| WO | 2011/094545 | A2 | 8/2011 | |
| WO | 2011/109059 | A1 | 9/2011 | |
| WO | 2012/163490 | A1 | 12/2012 | |
| WO | 2013/109199 | A1 | 7/2013 | |
| WO | 2013/178815 | A1 | 12/2013 | |
| WO | 2014/009936 | A1 | 1/2014 | |
| WO | 2014/031732 | A2 | 2/2014 | |
| WO | 2014/134127 | A1 | 9/2014 | |
| WO | 2014/167530 | A1 | 10/2014 | |
| WO | 2014/176542 | A1 | 10/2014 | |
| WO | 2014/179785 | A1 | 11/2014 | |

OTHER PUBLICATIONS

Aboul-Enein et al., Scavenging of reactive oxygen species by N-substituted indole-2 and 3-carboxamides. Luminescence. Jan.-Feb. 2004;19(1):1-7.

Amin, The role of mast cells in allergic inflammation. Respir Med. Jan. 2012;106(1):9-14.

CAS Registry No. 752254-85-6. 1 page, Sep. 30, 2015.

CAS Registry No. 875577-87-0. 1 page, Sep. 30, 2015.

Deli et al., Diabetic neuropathies: diagnosis and management. Neuroendocrinology. 2013;98(4):267-80.

Doupis et al., Microvascular reactivity and inflammatory cytokines in painful and painless peripheral diabetic neuropathy. J Clin Endocrinol Metab. Jun. 2009;94(6):2157-63.

Finn et al., Twenty-first century mast cell stabilizers. Br J Pharmacol. Sep. 2013;170(1):23-37.

Jeffcoate et al., Diabetic foot ulcers. Lancet. May 3, 2003;361(9368):1545-51.

Justad, Health and Medication Administration Manual for Individuals with Developmental Disabilities: A Self-Paced Study Guide and Reference Manual. vol. 7. Developmental Disability Program of the Department of Public Health and Human Services. 2009. Retrieved from the website: dphhs.mt.gov/Portals/85/dsd/documents/DDP/Home%20Page/MedicationCertificationManual.pdf. 220 pages, May 22, 2019.

Kraakman et al., Macrophage polarization in obesity and type 2 diabetes: weighing down our understanding of macrophage function? Frontiers in Immunology. Sep. 2014;5(470):1-6.

Liu et al., Genetic deficiency and pharmacological stabilization of mast cells reduce diet-induced obesity and diabetes in mice. Nat Med. Aug. 2009;15(8):940-5.

Machelska, Dual peripheral actions of immune cells in neuropathic pain. Arch Immunol Ther Exp (Warsz). Feb. 2011;59(1):11-24.

NCBI/MeSh, The MeSh definition of Topical administration. Retrieved online at: https://www.ncbi.nlm.nih.gov/mesh/?term=topical+administration. 2 pages, May 21, 2019.

Olgen et al., Antioxidant activity of N-substituted indole 2- and 3-carboxamides. Ankara Universitesi Eczacilik Fakultesi Dergisi. Jan. 2004;33(2):109-16.

Olgen et al., Syntheses and biological evaluation of indole-2 and 3-carboxamides: new selective cyclooxygenase-2 inhibitors. Pharmazie. Apr. 2002;57(4):238-42.

Olgen et al., Synthesis and evaluation of novel NZH and N-substituted indole-2- and 3-carboxamide derivatives as antioxidants agents. Journal of Enzyme Inhibition and Medicinal Chemistry. Aug. 2007;22(4):457-62.

Themistocleous et al., The clinical approach to small fibre neuropathy and painful channelopathy. Pract Neurol. Dec. 2014;14(6):368-79.

Theoharides et al., Mast cells and inflammation. Biochim Biophys Acta. Jan. 2012;1822(1):21-33.

Uemura et al., Diabetes mellitus enhances vascular matrix metalloproteinase activity: role of oxidative stress. Circ Res. Jun. 22, 2001;88(12):1291-8.

Vincent et al., Diabetic neuropathy: cellular mechanisms as therapeutic targets. Nat Rev Neurol. Sep. 13, 2011;7(10):573-83.

Wiggin et al., Elevated triglycerides correlate with progression of diabetic neuropathy. Diabetes. Jul. 2009;58(7):1634-40.

Zhang et al., Mast cell metabolic syndrome. Biochim Biophys Acta. Jan. 2012;1822(1):14-20.

Zuo et al., Inflammation and hyperalgesia induced by nerve injury in the rat: a key role of mast cells. Pain. Oct. 2003;105(3):467-79.

Bai et al., Structure-activity relationship study and discovery of indazole 3-carboxamides as calcium-release activated calcium channel blockers. Bioorg Med Chem Lett. Feb. 1, 2017;27(3):393-397.

U.S. Appl. No. 16/069,961, filed Jul. 13, 2018, 2019-0016680, Published.

U.S. Appl. No. 15/574,913, filed Nov. 17, 2017, 2018-0161388, Abandoned.

* cited by examiner

MAST-CELL MODULATORS AND USES THEREOF

RELATED APPLICATIONS

This application is a divisional of U.S. application Ser. No. 16/069,961, filed Jul. 13, 2018, which is a 35 U.S.C. § 371 national stage filing of International Application No. PCT/US2017/013279, filed on Jan. 13, 2017, which claims priority to U.S. Provisional Application No. 62/278,722, filed on Jan. 14, 2016. The entire contents of each of the foregoing applications are incorporated herein by reference in their entireties.

STATEMENT OF GOVERNMENT INTEREST

This invention was made with government support under Grant No. DK091949 awarded by the National Institutes of Health. The government has certain rights in the invention.

TECHNICAL FIELD

The present disclosure relates to mast cell (MC) modulators, processes for their preparation, pharmaceutical compositions containing these modulators, and their use in the treatment of diseases associated with mast cells.

BACKGROUND

Traditionally, mast cells have been known for their role in allergic and anaphylactic reactions, as well as their involvement in acquired and innate immunity, bacterial infections, and autoimmunity. See e.g., Respitory Medicine, Volume 106, Issue 1, pp. 9-14 (January 2012); Proc. Natl Acad. Sci. USA 102 (2005) 1578-1583; Nat. Immunol. 6 (2005) 135-142; Nature 432 (2004) 512-516; Eur. J. Immunol. 40 (2010) 1843-1851; Nat. Rev. Immunol. 10 (2010) 440-452; Autoimmun Rev. 4 (2005) 21-27; and Nat. Immunol. 11 (2010) 471-476. In addition to being associated with allergic inflammation (e.g., asthma, atopic dermatitis, allergic rhinitis and ocular allergic diseases), evidence now implicates mast cells with inflammatory diseases through non-allergic triggers as well as fibrosis, cancers, central nervous system disorders, and metabolic disorders. See e.g., Biochimica et Biophysica Acta, 1822 (2012) 21-23; DNA Cell Biol. 2013 April 32(4):206-18; Cancer Metastasis Rev. 2011 Mar. 30(1):45-60; Nature 210, 756-757 (14 May 1966); Biochimica et Biophys Acta. 212 January 1822(1):14-20; and Front Immunol. 2012; 3: 7.

Over the last decade or so it has also been shown that inflammation is a major factor of diabetic neuropathy (Nature reviews Neurology 2011; 7:573-83) Dyslipidemia (Diabetes 2009; 58:1634-40), LDL oxidation (Diabetes 2009; 58:2376-85), poly(ADP-ribose) activation (Free Radic Biol Med 2011; 50:1400-9). Increased levels of advanced glycated endproducts (AGEs) and their receptor RAGE (Diabetes 2013; 62:931-43) are the main causes for this increased inflammatory response (Diabetologia 2009; 52:2251-63). To this end, the role of local skin inflammation on the development of small fiber neuropathy (SFN), and the indentification of several new factors that play a role in development of SFN and diabetic peripheral neuropathy (DPN), such as e.g., the interaction among neuropeptides, mast cells and macrophages, and increased mast cell degranulation and M1 macrophage activation in diabetic models is described in U.S. Provisional Application No. 62/162,972.

Given the involvement of mast cells in a wide variety of therapeutic pathways and targets, it is therefore desirable to prepare compounds that modulate mast cells (e.g., mast cell stabilizers) and hence have utility for treating one or more conditions associated with mast cells.

SUMMARY

Figure 1:
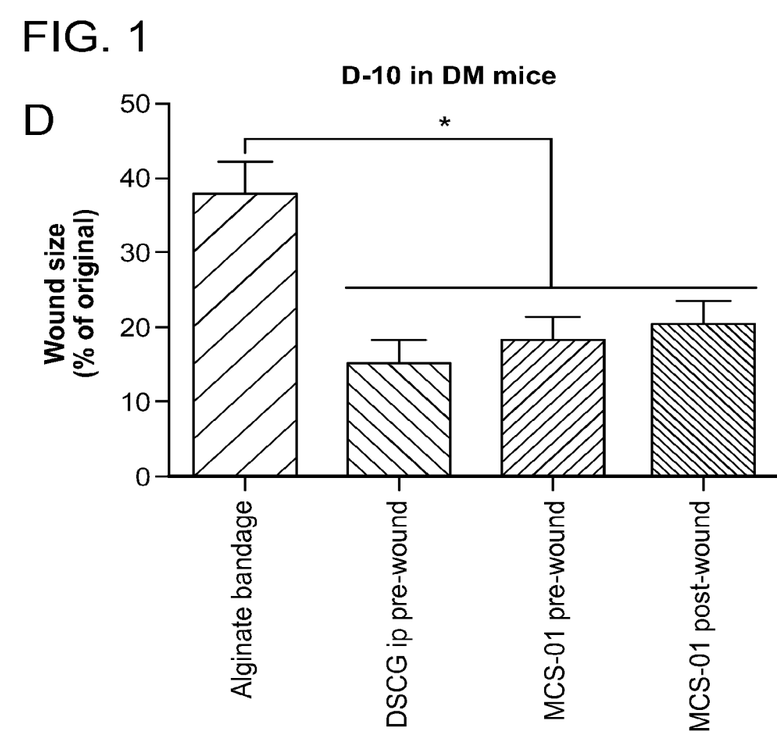
FIG. 1 illustrates the effects on would healing in diabetic mice from treatment of a compound described herein.

It has now been found that compounds described herein, and pharmaceutically acceptable compositions thereof, are effective modulators of mast cells and are useful in treating conditions associated therewith such as e.g., to promote wound healing in diabetic subjects (see e.g., FIG. 1). Such compounds include those of Formula I:

(I)

or a pharmaceutically acceptable salt thereof, wherein each of X, Y, Cy, $R^1$, $R^2$, s, and p are as defined and described herein.

The compounds described herein useful for treating a variety of diseases, disorders or conditions associated with mast cells. Such diseases, disorders, or conditions include those described herein.

DETAILED DESCRIPTION OF CERTAIN EMBODIMENTS

1. General Description of Compounds

In certain embodiments, the present disclosure provides a compound of Formula I:

3

(I)

or a pharmaceutically acceptable salt thereof, wherein
Z is CH or N;
X is CO and Y is NH, or X is NH and Y is CO;
Cy is phenyl or pyridyl;
$R^1$ and $R^2$ are each halo; and
p and s are each independently 1, 2, or 3; provided the compound is not or or a pharmaceutically acceptable salt thereof.

2. Compounds and Definitions

The terms "halo" and "halogen" as used herein refer to an atom selected from fluorine (fluoro, —F), chlorine (chloro, —Cl), bromine (bromo, —Br), and iodine (iodo, —I).

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The compounds of the herein may be present in the form of pharmaceutically acceptable salts. For use in medicines, the salts of the compounds of the invention refer to nontoxic "pharmaceutically acceptable salts." Pharmaceutically acceptable salt forms include pharmaceutically acceptable acidic/anionic or basic/cationic salts.

Pharmaceutically acceptable acidic/anionic salts include, but are not limited to the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

3. Description of Exemplary Compounds

In a first embodiment, the present disclosure provides a compound of Formula I:

(I)

or a pharmaceutically acceptable salt thereof, polymorph, or solvate thereof, wherein the variables are as described above. Alternatively, the present disclosure provides a compound of Formula I or a pharmaceutically acceptable salt thereof.

In a second embodiment, the compound of Formula I is of the Formula II or III:

(II) or (III)

or a pharmaceutically acceptable salt thereof, wherein the variables are as described above for Formula I.

In a third embodiment, the compound of Formula I is of the Formula IV or V:

or a pharmaceutically acceptable salt thereof, wherein the variables are as described above for Formula I and the second embodiment.

In a fourth embodiment, p in Formula I, II, III, IV, and V is 2, wherein the remaining variables are as described above for Formula I and the second or third embodiment.

In a fifth embodiment, s in Formula I, II, III, IV, and V is 1 or 2, wherein the remaining variables are as described above for Formula I and the second, third, or fourth embodiment.

In a sixth embodiment, $R^2$ in Formula I, II, III, IV, and V is fluoro, wherein the remaining variables are as described above for Formula I and the second, third, fourth, or fifth embodiment.

In a seventh embodiment, $R^1$ in Formula I, II, III, IV, and V is chloro, wherein the remaining variables are as described above for Formula I and the second, third, fourth, or fifth embodiment.

In an eighth embodiment, the compound of Formula I is selected from or a pharmaceutically acceptable salt thereof.

Specific examples of compounds are provided in the EXEMPLIFICATION. In some embodiments, a provided compound is one or more compounds selected from those exemplified in the EXEMPLIFICATION section below, or a pharmaceutically acceptable salt thereof. That is, pharmaceutically acceptable salts as well as the neutral forms of these compounds are included herein.

In other embodiments, the present disclosure provides a method of treating a subject (e.g., a human) with a condition associated with mast cells comprising the step of administering to the patient an effective amount of a compound of the Formula I, II, III, IV, and V, or a pharmaceutically acceptable salt or composition thereof. Conditions associated with mast cells include, but are not limited to, bacterial infections, allergic reactions, inflammatory diseases, fibrosis, cancers, central nervous system disorders, and metabolic disorders. Specific conditions include e.g., allograft rejection, diabetic retinopathy, choroidal neovascularization due to age-related macular degeneration, psoriasis, arthritis, osteoarthritis, rheumatoid arthritis, synovial pannus invasion in arthritis, multiple sclerosis, myasthenia gravis, diabetes mellitus, diabetic angiopathy, diabetic neuropathy, infantile hemangiomas, non-small cell lung, bladder and head and neck cancers, prostate cancer, breast cancer, ovarian cancer, gastric and pancreatic cancer, psoriasis, fibrosis, rheumatoid arthritis, atherosclerosis, restenosis, allergy, respiratory diseases, asthma, transplantation rejection, thrombosis, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, ocular disease, viral infection, heart disease, lung or pulmonary diseases or kidney or renal diseases, skin inflammation, and bronchitis.

In other embodiments, the present disclosure provides a method of delaying the onset of, reversing, or reducing the risk of acquiring peripheral neuropathy (PN) in a subject (e.g., a human) having diabetes, comprising administering to the subject an effective amount of a compound of the Formula I, II, III, IV, and V, or a pharmaceutically acceptable salt or composition thereof.

In other embodiments, the present disclosure provides a method of delaying the onset of, reversing, or reducing the risk of acquiring peripheral diabetic neuropathy (PN) in a subject (e.g., a human) in need thereof, comprising administering to the subject an effective amount of a compound of the Formula I, II, III, IV, and V, or a pharmaceutically acceptable salt or composition thereof.

In other embodiments, the present disclosure provides a method of delaying the onset of, reducing the risk of developing, or accelerating the healing of a wound in a subject (e.g., a human) having diabetes, comprising administering to the subject an effective amount of a compound of the Formula I, II, III, IV, and V, or a pharmaceutically acceptable salt or composition thereof.

In other embodiments, the present disclosure provides a method for altering the M1/M2 macrophage ratio in a wound on a subject (e.g., a human) having diabetes, comprising administering to the subject an effective amount of a compound of the Formula I, II, III, IV, and V, or a pharmaceutically acceptable salt or composition thereof.

In other embodiments, the present disclosure provides a method of preventing the increase of matrix metallopeptidase 9 (MMP-9), in a subject (e.g., a human) having diabetes, comprising administering to the subject an effective amount of a compound of the Formula I, II, III, IV, and V, or a pharmaceutically acceptable salt or composition thereof.

4. Uses, Formulation and Administration

According to another embodiment, the present disclosure provides a method of treating a subject (e.g., a human) with a condition associated with mast cells using a composition comprising a compound of the Formula I, II, III, IV, and V, or a pharmaceutically acceptable salt or composition thereof; and a pharmaceutically acceptable carrier, adjuvant, or vehicle. Disorders associated with mast cells are described above.

According to another embodiment, the present disclosure provides a method of delaying the onset of, reversing, or reducing the risk of acquiring peripheral neuropathy (PN) in a subject (e.g., a human) having diabetes, using a composition comprising a compound of the Formula I, II, III, IV, and V, or a pharmaceutically acceptable salt or composition thereof; and a pharmaceutically acceptable carrier, adjuvant, or vehicle.

According to another embodiment, the present disclosure provides a method of delaying the onset of, reversing, or reducing the risk of acquiring peripheral diabetic neuropathy (PN) in a subject (e.g., a human) in need thereof, using a composition comprising a compound of the Formula I, II, III, IV, and V, or a pharmaceutically acceptable salt or composition thereof; and a pharmaceutically acceptable carrier, adjuvant, or vehicle.

According to another embodiment, the present disclosure provides a method of delaying the onset of, reducing the risk of developing, or accelerating the healing of a wound in a subject (e.g., a human) having diabetes, using a composition comprising a compound of the Formula I, II, III, IV, and V, or a pharmaceutically acceptable salt or composition thereof; and a pharmaceutically acceptable carrier, adjuvant, or vehicle.

According to another embodiment, the present disclosure provides a method for altering the M1/M2 macrophage ratio in a wound on a subject (e.g., a human) having diabetes, using a composition comprising a compound of the Formula I, II, III, IV, and V, or a pharmaceutically acceptable salt or composition thereof; and a pharmaceutically acceptable carrier, adjuvant, or vehicle.

According to another embodiment, the present disclosure provides a method of preventing the increase of matrix metallopeptidase 9 (MMP-9), in a subject (e.g., a human)

having diabetes, using a composition comprising a compound of the Formula I, II, III, IV, and V, or a pharmaceutically acceptable salt or composition thereof; and a pharmaceutically acceptable carrier, adjuvant, or vehicle.

As used herein, delaying the onset of, reversing, or reducing the risk of acquiring, or reducing the risk of developing a condition recited herein (e.g., peripheral neuropathy (PN), small fiber neuropathy (SFN), and peripheral diabetic neuropathy) means decreasing the amount of mast cell degranulation in subjects who have elevated mast cell degranulation levels due to a condition/disease, such as e.g., diabetes. It has been found that subject having diabetes have an increase in mast cell degranulation. See e.g., U.S. Provisional Application No. 62/162,972.

As used herein, accelerating the healing of wound means that the compound of Formula I, II, III, IV, and V, or a pharmaceutically acceptable salt or composition thereof elicits a cellular environment that accelerates or promotes healing of the wound. For example, the he compound of Formula I, II, III, IV, and V, or a pharmaceutically acceptable salt or composition thereof may elicit the release of cytokines such as CXCL8, CCL2 and CXCL7, each of which are necessary for the first phase of wound healing, thereby promoting healing of a wound. The first phase of wound healing is the inflammatory phase that lasts for approximately three days and it is followed by the proliferative phase that lasts two to three weeks. In chronic wounds this linear progression is abolished and are characterized by the presence of low grade chronic inflammation. The application of the compound of Formula I, II, III, IV, and V, or a pharmaceutically acceptable salt or composition thereof can convert the chronic low grade inflammation to an intense acute inflammatory phase that then progresses to the proliferative phase and promotes wound healing.

In certain embodiments, the amount of compound of the Formula I, II, III, IV, and V in a provided composition is such that it is effective as a mast cell stabilizer (such as a mast cell degranulation inhibitor) in a biological sample or in a subject. In certain embodiments, a provided composition is formulated for administration to a subject in need of such composition. In some embodiments, a provided composition is formulated for oral administration to a subject. In other embodiments, a provided composition is formulated for topical administration to a subject.

The term "pharmaceutically acceptable carrier, adjuvant, or vehicle" refers to a nontoxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable compositions described herein may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Pharmaceutically acceptable compositions described herein may also be prepared in injectable form. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Pharmaceutically acceptable compositions described herein may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

The amount of compounds described herein that may be combined with the carrier materials to produce a composition in a single dosage form will vary depending upon the host treated and the particular mode of administration. In some embodiments, provided compositions should be formulated so that a dosage of between 0.01-100 mg/kg body weight/day of the inhibitor, such as e.g., 0.1-100 mg/kg body weight/day, can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the composition.

Unless specified otherwise, the terms "treatment," "treat," and "treating" refer to therapeutic treatment.

Modulation of mast cells (or to modulate mast cells) means that a change or alternation in the activity of mast cells has occurred from the administration of one or more of the compounds described herein. Modulation may be an upregulation (increase) or a downregulation (decrease) in the magnitude of the activity or function of mast cells. Exemplary activities and functions include e.g., binding characteristics, enzymatic activity, cell receptor activation, transcriptional activity, and signal transduction. In one aspect, the compounds described herein stabilize mast cells.

In further aspects, the compounds described herein act as mast cell degranulation inhibitors.

Exemplification

As depicted in the Examples below, in certain exemplary embodiments, compounds are prepared according to the following general procedures. It will be appreciated that, although the general methods depict the synthesis of certain compounds herein, the following general methods, and other methods known to one of ordinary skill in the art, can be applied to all compounds and subclasses and species of each of these compounds, as described herein.

General Description of Synthesis

The compounds described herein can be readily prepared according to the following reaction schemes and examples, or modifications thereof, using readily available starting materials, reagents and conventional synthesis procedures. In these reactions, it is also possible to make use of variants which are themselves known to those of ordinary skill in the art, but are not mentioned in greater detail. Furthermore, other methods for preparing compounds described herein will be readily apparent to a person of ordinary skill in the art in light of the following reaction schemes and examples.

For example, compound of Formula I where X is CO and Y is NH can be prepared by reacting a compound of Formula 100 with a compound of Formula 110 in an organic solvent (e.g., DMF) in the presence of base (e.g., NaH) to form a compound of Formula 120. See e.g., Scheme 1.

The compound of Formula I can then be formed by converting the carboxylic acid portion of the compound of Formula 120 to an activated group (such as an acid chloride via treatment with DMF and $(COCl)_2$ in DCM) followed by treatment with a compound of Formula 130 in the presence of base (e.g., TEA).

In an alternative, compounds of Formula I, where X is NH and Y is CO can be prepared by reacting a compound of Formula 140 with a compound of the Formula 110 in an organic solvent (e.g., DMF) in the presence of base (e.g., KOH) to form a compound of 150. See Scheme 3.

The compound of Formula I can then be formed by reacting amine 150 with a compound of the Formula 160 in the present an organic solvent (e.g., dichloromethane). See e.g., Scheme 4.

Scheme 4

Preparation of Compounds of Formula I

Reagents and solvents were purchased from commercially available sources and used without further purification. All reactions were carried out according to the indicated procedures and conditions. Reactions were monitored by LC/MS analysis and/or thin-layer chromatography (TLC) on silica-coated glass plates (EMD silica gel 60 F254) with the indicated eluent. The compounds were visualized by UV light (254 nm). LC/MS analysis was performed on an Agilent 1200 HPLC/UV (220 nm and/or 254 nm wavelength) system coupled with a mass spectroscopic (Applied Biosystems, MDS SCIEX, Q TRAP LC/MS/MS) detector. Compounds for analysis were dissolved in 100% DMSO and separated on C18 cartridge (particle size 2.6 m, dimensions: 100 mm×2.1 mm, 0.3 mL/min flow rate, 1 mL injection volume) using acetonitrile/water mobile phase with 0.1% formic acid as a modifier. The gradient started at 20% acetonitrile, held for 2 min, and linearly increased to 97% acetonitrile over 10 min, with 3 min hold at 97% acetonitrile and subsequent re-equilibration to the original conditions in a total of 17 min.

Compounds reported were obtained in a purity as >95% at 254 nm wavelength. Nuclear magnetic resonance ($^1$H NMR) spectra were recorded on a Varian Mercury plus NMR spectrometer operating at 400.13 MHz frequencies for 1H, using a 5 mm ASW PFG probe capable of detecting $^1$H, $^{13}$C, $^{31}$P, and $^{15}$N nuclei. The proton chemical shifts (ppm) were referenced to the tetramethylsilane internal standard (0 ppm). NMR data are reported with these descriptions: s, singlet; d, doublet; t, triplet; q, quartet; m, multiplet; br, broad peak.

Compounds of Formula I were prepared according to the general procedures outlined below.

Example 1

1-[(2,4-dichlorophenyl)methyl]-N-(2,6-difluorophenyl)indole-3-carboxamide

To a solution of indole (806 mg) in DMF (10 mL) was added portion-wise NaH (60% in mineral oil, 440 mg) at 0° C. The resulting suspension was further stirred at 0° C. to r.t. for 45 min. The resulting mix was cooled to 0° C. followed by the addition of 2,4-dichlorobenzyl chloride dropwise. The reaction mix was further stirred at 0° C. to r.t. and monitored by TLC. To the reaction mix was added MeOH, and was then acidified with 2N HCl. The precipitates were isolated by filtration to give the product as a yellow solid (1.57 g, 98%). $^1$H NMR $^1$H NMR (400 MHz, d-DMSO): δ 12.10 (br, 1H, acid-H), 8.12 (s, 1H), 8.02-8.08 (m, 1H), 7.71 (d, J=2.4 Hz, 1H), 7.42-7.48 (m, 1H), 7.35-7.38 (dd, J=2.4, 8.2 Hz, 1H), 7.19-7.23 (m, 2H), 6.80 (d, J=8.0 Hz, 1H), 5.58 (s, 2H, CH$_2$).

15

-continued

Compound 1

To a mix of the indole carboxylic acid (800 mg) and DCM (5 mL) was added oxalyl chloride (430 µL) followed by 1 drop of DMF. The reaction mix was stirred at r.t. for 30 min, and solvent was removed under vacuum to give a pink solid, which was added portion-wise into a solution of 2,6-difluoroaniline (538 µL) and triethylamine (697 µL) in DCM (5 mL) at r.t. The resulting mix was stirred at r.t. for overnight. The reaction mix was then poured into water (10 mL) and the crude product (800 mg) was collected by filtration and was further purified by flash chromatography to give the pure product 1-(2,4-dichlorobenzyl)-N-(2,6-difluorophenyl)-1H-indole-3-carboxamide, Compound 1 as a white solid. $^1$H NMR (400 MHz, d6-DMSO): δ 9.70 (s, 1H), 8.32 (s, 1H), 8.26 (d, J=7.4 Hz, 1H), 7.83 (d, J=2.0 Hz, 1H), 7.65 (d, J=7.8 Hz, 1H), 7.51-7.55 (dd, J=2.2, 8.4 Hz, 1H), 7.40-7.49 (m, 1H), 7.24-7.36 (m, 4H), 7.16 (d, J=8.61 Hz, 1H), 5.68 (s, 2H). $^{13}$C NMR: δ 163.0, 160.0, 157.5, 151.8, 136.8, 133.9(2), 133.8, 132.6, 131.4, 129.7, 128.4, 128.1, 127.2, 123.2, 121.9, 121.8, 112.3, 112.1, 111.1, 109.8, 47.4. MS (ESI+): 431.5 [M]$^+$, 433.4 [M+2]$^+$.

16

Example 2

N-[1-[(2,4-dichlorophenyl)methyl]indazol-3-yl]-2,6-difluoro-benzamide (2)

1H-indazol-3-amine (1.33 g, 10 mmol) was added to a prepared (pre-heated 60° C. for 1 h, stirred at room temperature overnight) brown suspension of crushed KOH (1.4 g, 25 mmol) in DMSO (200 mL) at room temperature. The resulting suspension was further stirred at ~r.t. for 30 min. 2,4-dichlorobenzyl chloride (1.74 mL, 12.5 mmol) was added in one portion. The reaction mix was further stirred at r.t. for 5 h. Water (300 mL) was added to the reaction mixture. The formed yellow precipitate was isolated by filtration. (2.2 g, 72% yield). $^1$H NMR (400 MHz, DMSO-d$_6$): δ 7.69 (d, J=8 Hz, 1H), 7.61 (d, J=1.6 Hz, 1H), 7.38 (d, J=8.4 Hz, 1H), 7.27-7.33 (m, 2H), 6.93 (t, J=7.2 Hz, 1H), 6.80 (d, J=8.8 Hz, 1H), 5.528 (s, br, 2H), 5.36 (s, 2H). MS (ESI+) m/z calc. for [C$_{14}$H$_{11}$Cl$_2$N$_3$] 291.03, Found [M+H]$^+$ 292.

To a solution of 2,6-difluorobenzoic acid (80 mg, 0.25 mmol) in DCM (1 mL) was added oxalyl chloride (32 µl, 0.38 mmol) and DMF (one drop) at r.t. The mixture was stirred for 30 min. 1[(2,4-dichlorophenyl)methyl]indazol-3-amine (73 mg, 0.25 mmol) was dissolved in DCM (1 mL) and TEA (53 µL, 0.38 mL) was added and also stirred for 30 min. Both solutions were cooled to −20° C. (10 min), combined and stirred for 1 h at −20° C. Methanol (2 ml) was added. Subsequently the pale yellow solution was added dropwise into water (8 mL). Hexanes was added (4 mL) and the solution was cooled to −20° C. overnight. The formed precipitate was washed with water and hexanes, dried under vacuum to afford the desired product $^1$H NMR (400 MHz, DMSO-d$_6$): δ 11.28 (s, 1H), 7.83 (d, J=8.4 Hz, 1H), 7.70 (d, J=8.4 Hz, 1H), 7.66 (d, J=2.0 Hz, 1H), 7.53-7.60 (m, 1H), 7.44 (dt, J=7.6 Hz, 1.2 Hz, 1H), 7.38 (dd, J=8.4 Hz, 2.0 Hz 1H), 7.14-7.26 (m, 3H), 6.96 (d, J=8.4 Hz, 1H), 5.67 (s, 2H, CH$_2$). MS (ESI+) m/z calc. for [C$_{21}$H$_{13}$Cl$_2$F$_2$N$_3$O] 431.04, Found 432.4 [M+H]$^+$.

Example 3

N-[1-[(2,4-dichlorophenyl)methyl]indazol-3-yl]-2-fluoro-benzamide (3)

The tile compound was prepared following the methods set forth in Example 2 with the appropriate starting materials. $^1$H NMR (400 MHz, CDCl$_3$): δ 9.11 (d, J=14 Hz, 1H), 8.24 (t, J=7.4 Hz, 1H), 8.12 (d, J=4.4 Hz, 1H), 7.98-8.04 (dt, J=7.6 Hz 1.2 Hz, 1H), 7.07-7.44 (m, 7H), 6.76 (d, J=8.4 Hz, 1H), 5.58 (s, 2H, CH$_2$). MS (ESI+) m/z calc. for [C$_{21}$H$_{13}$Cl$_2$F$_2$N$_3$O] 413.05, Found 414.5 [M+H]$^+$.

Example 4

N-[1-[(2,4-dichlorophenyl)methyl]indazol-3-yl]-3-fluoro-pyridine-4-carboxamide (4)

The tile compound was prepared following the methods set forth in Example 2 with the appropriate starting materials. $^1$H NMR (400 MHz, CDCl$_3$): δ 8.93 (d, J=12.8 Hz, 1H), 8.70 (d, J=2.4 Hz, 1H), 8.67 (dd, J=4.8 Hz, 0.8 Hz, 1H), 8.05-8.13 (m, 2H), 7.43 (d, J=2.4 Hz, 1H), 7.39-7.43 (m, 1H), 7.32 (d, J=8.8 Hz, 1H), 7.22 (t, J=7.6 Hz, 1H), 7.12 (dd, J=2.0, 8.4 Hz, 1H), 6.77 (d, J=8.4 Hz, 1H), 5.59 (s, 2H, CH$_2$). MS (ESI+) m/z calc. for [C$_{20}$H$_{13}$Cl$_2$FN$_4$O] 414.04, Found 415.5 [M+H]$^+$.

Example 5

N-[1-[(2,4-dichlorophenyl)methyl]indazol-3-yl]-3,5-difluoro-pyridine-4-carboxamide (5)

The tile compound was prepared following the methods set forth in Example 2 with the appropriate starting materials. $^1$H NMR (400 MHz, CDCl$_3$): δ 8.52 (s, 2H), 8.15 (d, J=8.0 Hz, 1H), 7.40-7.46 (m, 1H), 7.32 (d, J=8.4 Hz, 1H), 7.22 (d, J=7.2 Hz, 1H), 7.10 (dd, J=2.0, 8.8 Hz, 1H), 6.74 (d, J=8.0 Hz, 1H), 5.55 (s, 2H, CH$_2$). MS (ESI+) m/z calc. for [C$_{20}$H$_{12}$Cl$_2$F$_2$N$_4$O] 432.04, Found 433.5 [M+H]$^+$.

Example 6

N-[1-[(2,4-dichlorophenyl)methyl]indazol-3-yl]-2,4-difluoro-benzamide (6)

The tile compound was prepared following the methods set forth in Example 2 with the appropriate starting materials. $^1$H NMR (400 MHz, DMSO-d$_6$): δ 10.87 (s, 1H), 7.82 (d, J=8.0 Hz, 2H), 7.65-7.70 (m, 2H), 7.36-7.45 (m, 3H), 7.12-7.23 (m, 2H), 7.96 (d, J=8.0 Hz, 2H), 5.65 (s, 2H, CH$_2$). MS (ESI+) m/z calc. for [C$_{21}$H$_{13}$Cl$_2$F$_2$N$_3$O] 431.04, Found 432.4 [M+H]$^+$.

Example 7

1-[(2,4-dichlorophenyl)methyl]-N-(2,6-difluorophenyl)indazole-3-carboxamide (7)

The tile compound was prepared following the methods set forth in Example 1 with the appropriate starting materials. $^1$H NMR (400 MHz, DMSO-d$_6$): δ 10.06 (s, 1H, amide), 8.20 (s, 1H), 7.81 (d, J=8.8 Hz, 1H), 7.72 (d, J=2.4 Hz, 1H), 7.52 (t, J=8.0 Hz, 1H), 7.34-7.41 (m, 3H), 7.20 (t, J=8.0 Hz, 2H), 6.88 (d, J=8.4 Hz, 1H), 5.90 (s, 2H, CH$_2$). MS (ESI+) m/z calc. for [C$_{21}$H$_{13}$Cl$_2$F$_2$N$_3$O] 431.04, Found 432.5 [M+H]$^+$.

Example 9

N-(2-chloro-6-fluoro-phenyl)-1-[(2,4-dichlorophenyl)methyl]indazole-3-carboxamide (8)

The tile compound was prepared following the methods set forth in Example 1 with the appropriate starting materials. $^1$H NMR (400 MHz, CDCl$_3$): δ 8.48 (s, 1H), 8.42 (d, J=8.0 Hz, 1H), 7.19-7.47 (m, 6H), 7.11-7.16 (m, 2H), 6.76 (d, J=8.0 Hz, 1H), 5.72 (s, 2H, CH$_2$). MS (ESI+) m/z calc. for [C$_{21}$H$_{13}$Cl$_3$FN$_3$O] 447.01, Found 448.5 [M+H]$^+$.

Example 10

1-(2,4-dichlorobenzyl)-N-(3-fluoropyridin-4-yl)-1H-indole-3-carboxamide (9)

The tile compound was prepared following the methods set forth in Example 1 with the appropriate starting materials. $^1$H NMR (400 MHz, DMSO-d$_6$): δ 9.56 (s, 1H, amide), 8.29 (s, 2H), 816-8.20 (m, 1H), 7.72 (d, J=2.4 Hz, 1H), 7.65-7.71 (m, 1H), 7.52 (d, J=7.6 Hz, 1H), 7.41 (dd, J=2.0, 8.4 Hz, 1H), 7.16-7.29 (m, 4H), 7.00 (d, J=8.4 Hz, 1H), 5.57 (s, 2H, CH$_2$). MS (ESI+) m/z calc. for [C$_{22}$H$_{15}$Cl$_2$FN$_2$O] 412.05, Found 413.4 [M+H]$^+$.

Example 11

1-[(2,4-dichlorophenyl)methyl]-N-(2-fluorophenyl)indazole-3-carboxamide (10)

The tile compound was prepared following the methods set forth in Example 1 with the appropriate starting materials. $^1$H NMR (400 MHz, DMSO-d$_6$): δ 9.78 (s, 1H, amide), 8.29 (s, 2H), 8.24 (d, J=7.6 Hz, 1H), 7.84-7.90 (m, 1H), 7.80 (d, J=8.0 Hz, 1H), 7.70 (d, J=1.6 Hz, 1H), 7.51 (t, J=7.2 Hz, 1H), 7.34-7.39 (m, 1H), 7.25-7.34 (m, 1H), 7.20-7.24 (m, 1H), 6.91 (d, J=8.4 Hz, 1H), 5.88 (s, 2H, CH$_2$). MS (ESI+) m/z calc. for [C$_{21}$H$_{14}$Cl$_2$FN$_3$O] 413.05, Found 413.4 [M+H]$^+$.

Example 12

1[(2,4-dichlorophenyl)methyl]-N-(3-fluoro-4-pyridyl)indole-3-carboxamide (11)

The tile compound was prepared following the methods set forth in Example 1 with the appropriate starting materials. $^1$H NMR (400 MHz, DMSO-d$_6$): δ 10.04 (s, 1H), 8.62 (d, J=2.8 Hz, 1H), 8.43 (s, 1H), 8.35 (d, J=6.0 Hz, 1H), 8.12-8.21 (m, 2H), 7.67 (d, J=2.0 Hz, 1H), 7.46-7.50 (m, 1H), 7.35 (dd, J=2.0, 8.4 Hz, 1H), 7.16-7.24 (m, 2H), 6.92 (d, J=8.8 Hz, 1H), 5.55 (s, 2H, CH$_2$). MS (ESI+) m/z calc. for [C$_{21}$H$_{14}$Cl$_2$FN$_3$O] 413.05, Found 414.4 [M+H]$^+$.

Example 13

N-[1-[(2,4-dichlorophenyl)methyl]indazol-3-yl]-3-fluoro-pyridine-4-carboxamide (12)

The tile compound was prepared following the methods set forth in Example 2 with the appropriate starting materials. $^1$H NMR (400 MHz, CDCl$_3$): δ 9.27 (s, 1H, amide), 8.60 (t, J=6.4 Hz, 1H), 8.48 (s, 1H), 8.38-8.44 (m, 1H), 7.36-7.50 (m, 4H), 7.14 (dd, J=2.0, 8.4 Hz, 1H), 6.75 (d, J=8.0 Hz, 1H), 5.75 (s, 2H, CH$_2$). MS (ESI+) m/z calc. for [C$_{20}$H$_{13}$Cl$_2$FN$_4$O] 414.04, Found 415.5 [M+H]$^+$.

Example 14

1-[(2,4-dichlorophenyl)methyl]-N-(2,4-difluorophenyl)indole-3-carboxamide (13)

The tile compound was prepared following the methods set forth in Example 2 with the appropriate starting materials. $^1$H NMR (400 MHz, DMSO-d$_6$): δ 9.60 (d, J=3.2 Hz, 1H, amide), 8.25 (d, J=5.2 Hz, 1H), 8.14-8.19 (m, 1H), 7.68-7.76 (m, 1H), 7.58-7.66 (m, 1H), 7.46-7.56 (m, 1H), 7.36-7.45 (m, 1H), 7.26-7.35 (m, 1H), 7.14-7.25 (m, 2H), 7.03-7.12 (m, 1H), 6.96-7.03 (m, 1H), 5.56 (s, 2H, CH$_2$). MS (ESI+) m/z calc. for [C$_{22}$H$_{14}$Cl$_2$F$_2$N$_2$O] 430.04, Found 431.4 [M+H]$^+$.

Example 15

1-[(2,4-dichlorophenyl)methyl]-N-(2,4-difluorophenyl)indazole-3-carboxamide (14)

The tile compound was prepared following the methods set forth in Example 1 with the appropriate starting materials. $^1$H NMR (400 MHz, DMSO-d$_6$): δ 9.91 (s, 1H), 8.21 (d, J=8.0 Hz, 1H), 7.69-7.82 (m, 3H), 7.47-7.53 (m, 1H), 7.31-7.40 (m, 3H), 7.06-7.14 (m, 1H), 6.88 (d, J=8.8 Hz, 1H), 5.88 (s, 2H, CH$_2$). MS (ESI+) m/z calc. for [C$_{21}$H$_{13}$Cl$_2$F$_2$N$_3$O] 431.04, Found 432.4 [M+H]$^+$.

Example 16

1-[(2,4-dichlorophenyl)methyl]-N-(3,5-difluoro-4-pyridyl)indazole-3-carboxamide (15)

The tile compound was prepared following the methods set forth in Example 1 with the appropriate starting materials. $^1$H NMR (400 MHz, DMSO-d$_6$): δ 10.52 (s, 1H, amide), 8.60 (s, 2H), 8.19 (d, J=8.8 Hz, 1H), 7.81 (d, J=8.8 Hz, 1H), 7.71 (d, J=2.4 Hz, 1H), 7.50-7.55 (m, 1H), 7.34-7.40 (m, 2H), 6.86 (d, J=8.4 Hz, 1H), 5.91 (s, 2H, CH$_2$). MS (ESI+) m/z calc. for [C$_{20}$H$_{12}$Cl$_2$F$_2$N$_4$O] 432.04, Found 433.5 [M+H]$^+$.

Example 17

1-[(2-chlorophenyl)methyl]-N-(2,6-difluorophenyl)indole-3-carboxamide (16)

The tile compound was prepared following the methods set forth in Example 1 with the appropriate starting materials. $^1$H NMR (400 MHz, DMSO-d$_6$): δ 9.61 (s, 1H), 8.25 (s, 1H), 8.16 (d, J=7.2 Hz, 1H), 7.50-7.58 (m, 2H), 7.27-7.40 (m, 3H), 7.13-7.06 (m, 4H), 7.05 (dd, J=7.6 Hz, 1.6 Hz, 1H), 5.59 (s, 2H). MS (ESI+) m/z calc. for [C$_{22}$H$_{15}$ClF$_2$N$_2$O] 396.08, Found 397.5 [M+H]$^+$.

Example 18

1-[(4-chlorophenyl)methyl]-N-(2,6-difluorophenyl)indole-3-carboxamide (17)

The tile compound was prepared following the methods set forth in Example 1 with the appropriate starting materials. $^1$H NMR (400 MHz, DMSO-d$_6$): δ 9.61 (s, 1H), 8.32 (s, 1H), 8.13 (d, J=6.8 Hz, 1H), 7.55 (d, J=8.0 Hz, 1H), 7.26-7.44 (m, 5H), 7.13-7.24 (m, 4H), 5.12 (s, 2H). MS (ESI+): MS m/z calc. for [C$_{22}$H$_{15}$ClF$_2$N$_2$O] 396.08, Found 397.4 [M+H]$^+$.

Example 19

1-[(2,6-dichlorophenyl)methyl]-N-(2,6-difluorophenyl)indole-3-carboxamide (18)

The tile compound was prepared following the methods set forth in Example 1 with the appropriate starting materials. $^1$H NMR (400 MHz, DMSO-d$_6$): δ 9.56 (s, 1H), 8.16 (d, J=7.6 Hz, 1H), 7.91 (s, 1H), 7.73 (d, J=6.8 Hz, 1H), 7.65 (d, J=7.6 Hz, 2H); 7.53 (dd, J=8.4 Hz, 7.6 Hz, 1H) (s, 1H), 7.27-7.34 (m, 2H), 7.13-7.22 (m, 3H), 5.28 (s, 2H), MS (ESI+) m/z calc. for [C$_{22}$H$_{14}$Cl$_2$F$_2$N$_2$O]: 431.26; Found: 432.4 [M+H]$^+$.

Example 20

N-[1-[(2,4-dichlorophenyl)methyl]indazol-3-yl]-4-methyl-thiadiazole-5-carboxamide (19)

The tile compound was prepared following the methods set forth in Example 2 with the appropriate starting materials. $^1$H NMR (400 MHz, DMSO-d$_6$): δ 11.39 (s, 1H), 7.82 (d, J=8.4 Hz, 1H), 7.72 (d, J=8.8 Hz, 1H), 7.66 (d, J=2.0 Hz, 1H), 7.42-7.47 (m, 1H), 7.37-7.40 (dd, J=2.0, 8.4 Hz, 1H), 7.16 (t, J=7.4 Hz, 1H), 7.00 (d, J=8.0 Hz, 1H), 5.67 (s, 2H, CH$_2$), 2.83 (s, 3H, CH$_3$). MS (ESI+) m/z calc. for [C$_{19}$H$_{14}$Cl$_2$N$_4$OS] 416.03, Found 417.5 [M+H]$^+$.

Example 21

N-[1-[(2,4-dichlorophenyl)methyl]indazol-3-yl]-3-methyl-pyridine-4-carboxamide (20)

1H-indazol-3-amine (1.33 g, 10 mmol) was added to a prepared (pre-heated 60° C. for 1 h, stirred at room temperature overnight) brown suspension of crushed KOH (1.4 g, 25 mmol) in DMSO (200 mL) at room temperature. The resulting suspension was further stirred at ~r.t. for 30 min. 2,4-dichlorobenzyl chloride (1.74 mL, 12.5 mmol) was added in one portion. The reaction mix was further stirred at r.t. for 5 h. Water (300 mL) was added to the reaction mixture. The formed yellow precipitate was isolated by filtration. (2.2 g, 72% yield). $^1$H NMR (400 MHz, DMSO-d$_6$): δ 7.69 (d, J=8 Hz, 1H), 7.61 (d, J=1.6 Hz, 1H), 7.38 (d, J=8.4 Hz, 1H), 7.27-7.33 (m, 2H), 6.93 (t, J=7.2 Hz, 1H), 6.80 (d, J=8.8 Hz, 1H), 5.528 (s, br, 2H), 5.36 (s, 2H). MS (ESI+) m/z calc. for [C$_{14}$H$_{11}$Cl$_2$N$_3$] 291.03, Found [M+H]$^+$ 292.

To a solution of 3-methylpyridine-4-carboxylic acid (80 mg, 0.25 mmol) in DCM (1 mL) was added oxalyl chloride (32 μl, 0.38 mmol) and DMF (one drop) at r.t. The mixture was stirred for 30 min. 1[(2,4-dichlorophenyl)methyl]indazol-3-amine (73 mg, 0.25 mmol) was dissolved in DCM (1 mL) and TEA (53 μL, 0.38 mL) was added and also stirred for 30 min. Both solutions were cooled to −20° C. (10 min), combined and stirred for 1 h at −20° C. Methanol (2 ml) was added. Subsequently the pale yellow solution was added dropwise into water (8 mL). Hexanes was added (4 mL) and the solution was cooled to −20° C. overnight. The formed precipitate was washed with water and hexanes, dried under vacuum to afford the desired product 20 (78 mg, 76% yield). $^1$H NMR (400 MHz, DMSO-d$_6$): δ 11.01 (s, 1H), 8.55 (s, 1H), 8.52 (d, J=5.2 Hz, 1H), 7.84 (d, J=8.8 Hz, 1H), 7.66-7.71 (m, 2H), 7.50 (d, J=5.6 Hz, 1H), 7.36-7.46 (m, 2H), 7.16 (t, J=7.2 Hz, 1H), 6.97 (d, J=8.4 Hz, 1H), 5.67 (s, 2H, CH$_2$), 2.42 (s, 3H, CH$_3$). MS (ESI+) m/z calc. for [C$_{21}$H$_{16}$Cl$_2$N$_4$O] 410.07, Found 411.5 [M+H]$^+$.

Example 22

1-[(2,4-dichlorophenyl)methyl]-N-(thiadiazol-5-yl)indazole-3-carboxamide (21)

The tile compound was prepared following the methods set forth in Example 1 with the appropriate starting materials. $^1$H NMR (400 MHz, DMSO-d$_6$): δ 12.89 (s, 1H), 8.84 (s, 1H), 8.24 (d, J=8.0 Hz, 1H), 7.78 (d, J=8.0 Hz, 1H), 7.67 (d, J=2.4 Hz, 1H), 7.48-7.53 (m, 1H), 7.35-7.40 (m, 1H), 7.30 (dd, J=8.4 Hz 2.0 Hz, 1H), 6.74 (d, J=8.4 Hz, 1H), 5.90 (s, 2H, CH$_2$). MS (ESI+) m/z calc. for [C$_{17}$H$_{11}$Cl$_2$N$_5$OS] 403.01, Found 404.4 [M+H]$^+$.

Example 23

N-(2,6-difluorophenyl)-1-[[2-(trifluoromethoxy)phenyl]methyl]indole-3-carboxamide (22)

Prepared by following general procedure B. $^1$H NMR (400 MHz, DMSO-$d_6$): δ 9.61 (s, 1H), 8.27 (s, 1H), 8.15 (d, J=7.0 Hz, 1H), 7.44-7.51 (m, 3H), 7.33-7.37 (m, 2H), 7.10-7.24 (m, 5H), 5.58 (s, 2H), MS (ESI+) m/z calc. for [$C_{23}H_{15}F_5N_2O_2$]: 446.37; Found: 447.4 [M+H]$^+$.

1-(2,4-dichlorobenzyl)-N-(2-fluorophenyl)-1H-indole-3-carboxamide

The title compound can be prepared following the procedures set forth above.

Biological Data

General Procedures

Measurement of Intracellular $Ca^{2+}$ Concentration

RBL-2H3 cells (ATCC) were seeded in 96-well plate at $4\times10^4$ cells per well in DMEM-supplemented with 2% FBS and allowed to adhere overnight. Culture medium was then replaced with 50 µl of $Ca^{2+}$-free Tyrode solution to load $Ca^{2+}$-probe Fluo-4NW (Molecular Probe, Thermo Fisher, MA, USA) at 1:1 to the cells. New compound at indicated concentration was supplied during the probe loading from the beginning. Cells were incubated in the presence or absence of new compound for 60 minutes in the $Ca^{2+}$-free medium at 37° C. During the last 5 minutes of incubation, cells were treated with 1 µM thapsigargin (Sigma Aldrich) to deplete [$Ca^{2+}$]$_{ER}$. 20 mM $CaCl_2$ in saline solution was supplemented back to the [$Ca^{2+}$]$_{ER}$-depleted cells to be 2 mM as final. Cell medium was removed 1 minute after $Ca^{2+}$ reloading, and changes in Fluo-4NW fluorescence (RFU) were recorded with the multi-mode plate reader (FilterMax F5, Molecular Devices/Thermo Fisher Scientific, MA, USA) at an excitation wavelength of 485 nm and an emission wavelength of 535 nm.

Nuclear NFAT, Degranulation and Cytokine Release

[$Ca^{2+}$]$_{ER}$ in RBL2H3 cells were depleted by Tg in the same manner in the presence of the CRAC channel blockers as for [$Ca^{2+}$]$_i$ measurement but without loading the cells with Fluo-4NW. Then 200 µl of DMEM-3% FBS (containing 3 mM $Ca^{2+}$) was supplemented back in the presence of the corresponding concentration of CRAC channel blockers. Thirty minutes after $Ca^{2+}$-add back culture supernatant was collected for degranulation measurement. Degranulation was measured as secreted β-hexosaminidase according to the protocol of the assay kit (Sigma-Aldrich, MO, USA). Nuclear fraction was prepared from the cells for NFAT by using a subcellular protein fractionation kit (NE-PER™ Nuclear and Cytoplasmic Extraction Reagents, Pierce Biotechnology, Thermo Fisher Scientific, MA, USA). Nuclear NFAT-c1 was measured with an ELISA kit (Active Motif, CA, USA). At this time point TNFα was measured as pre-stored release with ELISA kits (R&D Systems, MN, USA). In a part after $Ca^{2+}$ add back incubation was prolonged for 4 h to measure de novo production of the cytokine TNFα.

Cytotoxicity

Toxicity was tested in RBL-2H3 cells. Cells were seeded in 96-well plate at $4\times10^4$ cells per well in DMEM-supplemented with 2% FBS and allowed to adhere overnight. Cells were then exposed to MCS compound at indicated concentrations for 4 h. Cell viability was determined by using counting assay (CCK8 cell counting kit, Dojindo Molecular Technologies, MD, USA).

Data Analyses.

$IC_{50}$ and $EC_{50}$ were calculated by nonlinear regression using Prims Graphpad software. Statistical analysis was performed by one-way ANOVA and post-hoc test (Tukey's test).

Inhibitory Activity

Inhibitory activity of calcium influx by the described compounds was determined using the RBL-2H3 rodent MC cell line as the primary in vitro assay. RBL-2H3 cells are known to express functional CRAC channel. Thapsigargin (Tg) is a sarco/endoplasmic reticulum (ER) $Ca^{2+}$-ATPase (SERCA) inhibitor that selectively activates the CRAC channels by depleting $Ca^{2+}$ in the ER store ([$Ca^{2+}$]$_{ER}$). Fluo-4NW was used as the molecular sensor to detect the concentration of intracellular calcium ([$Ca^{2+}$]$_i$). Under these assay conditions, approximately 3.5-fold higher [$Ca^{2+}$]$_i$ was consistently observed in RBL cells treated with Tg (1 µM) than that in untreated resting MCs. $IC_{50}$ results are shown in Table 1.

TABLE 1

| Compound | $IC_{50}$ (µM) |
| --- | --- |
| 1 | <10 |
| 2 | >30 |
| 3 | 29.0 |
| 4 | >30 |
| 5 | >30 |
| 6 | >30 |
| 7 | <10 |
| 8 | <10 |
| 9 | >30[b] |
| 10 | >30[b] |
| 11 | <10 |
| 12 | <10 |
| 13 | >30 |
| 14 | <10 |
| 15 | >30[b] |
| 16 | >30 |
| 17 | >30 |
| 18 | <30 |
| 19 | >30[b] |
| 20 | >30[b] |
| 21 | >30 |
| 22 | >30 |

Figure 3:
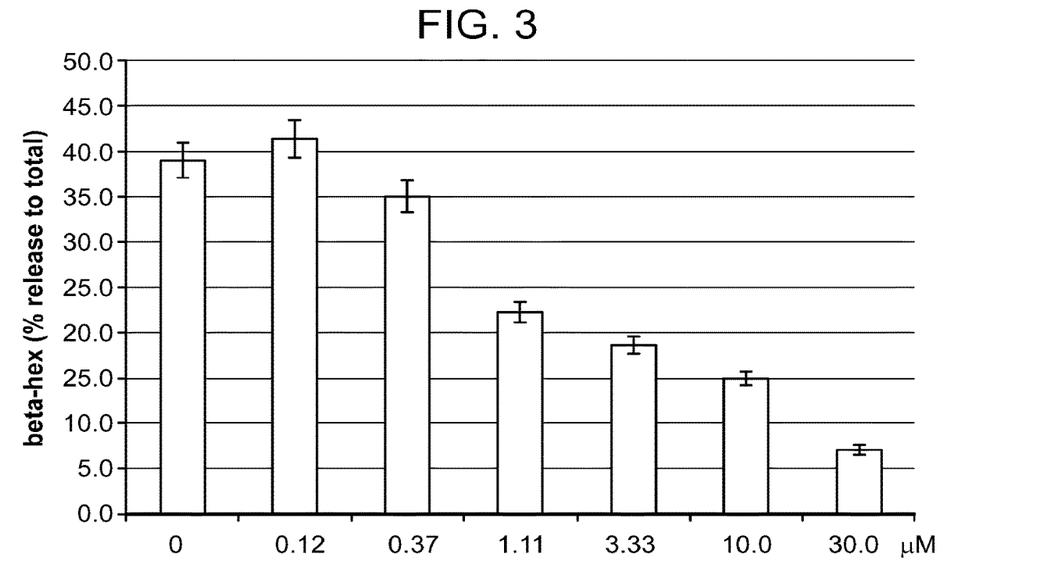
FIG. 3 shows dose-dependent inhibition by compound 12 of β-hex release from activated mast cells. Released β-Hex in cell culture supernatant were measured and compared with total β-Hex in cell lyses (reported as %).

Compound 12 was used to determine the inhibition of MC degranulation by measuring the release of pre-stored β-hexosaminidase (β-hex) upon MC activation. In the absence or presence of various concentrations of compound 12, RBL-2H3 cells were activated with the treatment of 1 µM thapsigargin in $Ca^{2+}$ free culture. 30 Minutes after assay media were replenished with extracellular $Ca^{2+}$, supernatants and cell lysates were analyzed for β-hex concentrations by ELISA. The ratio between the β-hex in supernatants and the total amount of β-hex (in supernatant plus cell lysates) indicated compound 12 significantly and dose-dependently inhibited the release of β-hex (See FIG. 3). In the absence of a CRAC inhibitor, 40% of β-hex was released, while compound 12 showed nearly complete inhibition of β-hex release at the highest concentration tested.

Figure 4:
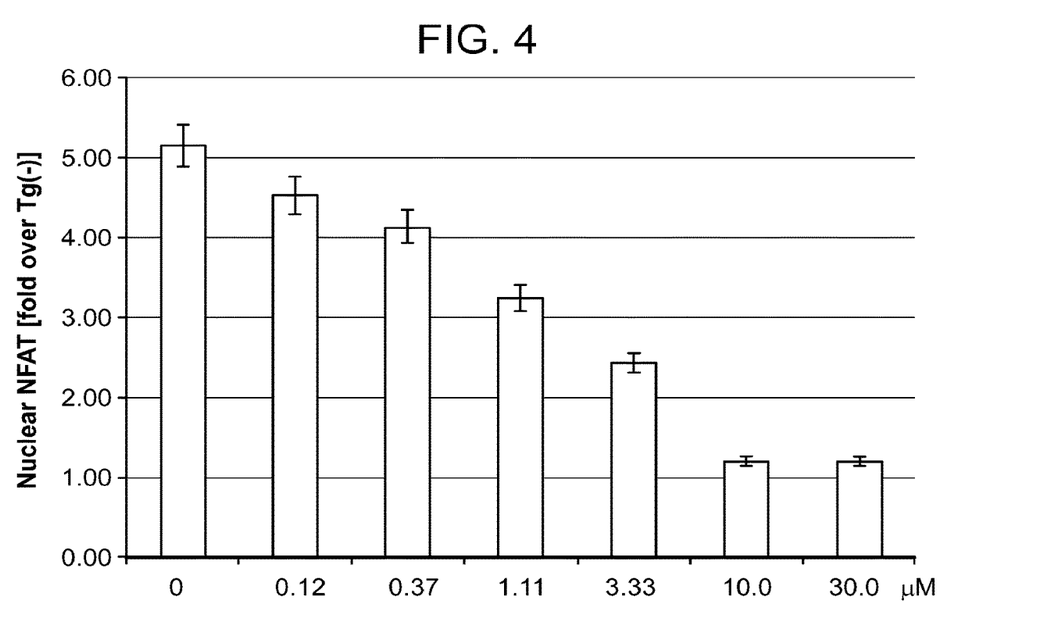
FIG. 4 shows dose-dependent inhibition by compound 12 of nuclear translocation of NFAT in activated mast cells.

The inhibition of nuclear translocation of the nuclear factor of activated T-cells (NFAT) by compound 12 in activated MCs was determined. The nuclear factor NFAT is a master regulator of numerous cytokines including TNFα. Cytosolic NFAT is dephosphorylated by the phosphatase calcineurin, which leads to the nuclear translocation of NFAT and subsequent gene activations for the expression of the corresponding cytokines. RBL cells were first treated with 1 µM thapsigargin in $Ca^{2+}$ free culture in the absence or presence of various concentrations of compound 12, which was followed by replenishing with extracellular $Ca^{2+}$ for 30 minutes. Nuclear fraction was prepared from the cells by subcellular protein fractionation, and the nuclear NFAT-c1 content was measured by ELISA. The fold increases of nuclear NFAT in activated MC as compared to that in resting MCs indicate the levels of MC activation. In the absence of CRAC channel blockers, we observed a 5-fold increase of nuclear NFAT in activated MCs, and compound 12 significantly and dose-dependently reduced the nuclear fraction of NFAT-c1 in activated RBL cells (FIG. 4). Further, at 10 µM and higher concentrations, compound 12 was able to restore the levels of nuclear NFAT to that of resting MCs.

Certain compounds were selected and demonstrated dose-dependent inhibition of the production of TNFα protein by activated MCs. Mast cells can secrete pre-stored TNFα immediately upon activation, as well as de novo synthesized TNFα that takes a few hours to produce. RBL cells were activated similarly as described above, in the presence of various concentrations of a CRAC channel blocker. 4 Hours after RBL cells were re-exposed to $Ca^{2+}$, secreted TNFα (which accounted for the combined protein from pre-stored and de novo synthesized TNFα) in the supernatants were measured by ELISA. Compounds showed dose-dependent inhibition of TNFα protein secretions (Table 2).

TABLE 2

| Compound | $IC_{50}$ (µM) TNFα |
| --- | --- |
| 7 | 0.47 |
| 8 | 0.74 |
| 11 | 0.58 |
| 12 | 0.28 |
| 14 | 0.64 |
| 15 | 0.14 |

Wound Healing in Diabetic Mice

C57B16 mice were made diabetic (DM) using Streptozotocin (STZ) and rabbits were made DM using alloxan. A 10-day wound-healing period was chosen since at least 80% wounds in non-DM mice and rabbits heal by that time-point. A dressing based on an alginate bandage for topical sustained release of Compound 1 was generated following the methods described in WO 2014/169250, and was then applied the shaved dorsum of DM mice either before (pre-wound) or after wounds (post-wound) were introduced. A comparison was made with the FDA-approved MC stabilizer, disodium cromoglycate (DSCG), 50 mg/kg DSCG (Intraperitoneal (ip) daily, 10 consecutive days prior to wounding) in non-DM and DM mice followed by wound procedure. Wound healing was monitored for 10 days.

Figure 2:
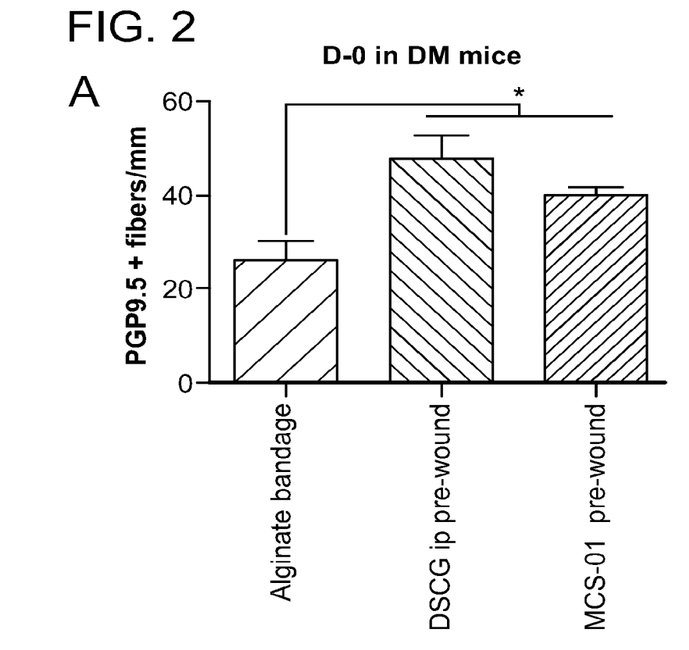
FIG. 2 illustrates the effects on the M1/M2 ratio in intact skin of diabetic mice from treatment with a compound described herein.

As expected, daily ip injection of DSCG improved diabetic mouse wound healing. See FIG. 1, *p<0.05. However, it was also found that topical application of Compound 1 (either for 10 days pre-wounding or for 10 days post-wounding) improved wound healing similar to systemic DSCG pre-treatment. See FIG. 1. Additionally, in the skin of DM mice, treatment with Compound 1 for 10 days without any wound increased the number of M2 macrophages. See FIG. 2. Similarly, DSCG treatment reduced M1/M2 ratio in intact skin. Without wishing to be bound by theory, these latter results suggest that MC stabilizers promote M1/M2 ratio reduction most likely by increasing M2.

While we have described a number of embodiments, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A method of delaying the onset of, reversing, or reducing the risk of acquiring peripheral neuropathy (PN) in a subject having diabetes, comprising administering to the subject an effective amount of a compound having the Formula:

or a pharmaceutically acceptable salt thereof, polymorph, or solvate thereof.

2. The method of claim 1, wherein the peripheral neuropathy is peripheral diabetic neuropathy.

3. A method of accelerating the healing of a wound in a subject having diabetes, comprising administering to the subject an effective amount of a compound having the Formula:

or a pharmaceutically acceptable salt thereof, polymorph, or solvate thereof.

* * * * *